United States Patent

Matsuzawa

[11] Patent Number: 6,159,233
[45] Date of Patent: Dec. 12, 2000

[54] SURGICAL NEEDLE DEVICE

[75] Inventor: Yuichi Matsuzawa, Ohmiya, Japan

[73] Assignee: Mani, Inc., Tochigi-ken, Japan

[21] Appl. No.: 08/945,414

[22] PCT Filed: Jan. 7, 1997

[86] PCT No.: PCT/JP97/00011

§ 371 Date: Oct. 30, 1997

§ 102(e) Date: Oct. 30, 1997

[87] PCT Pub. No.: WO98/30154

PCT Pub. Date: Jul. 16, 1998

[51] Int. Cl.[7] .................................................. A61B 17/06
[52] U.S. Cl. ............................................................ 606/223
[58] Field of Search ............................. 606/223, 224–227

[56] References Cited

U.S. PATENT DOCUMENTS

| | | | |
|---|---|---|---|
| 4,821,717 | 4/1989 | Wehrli | 606/223 X |
| 5,123,910 | 6/1992 | Mcintosh | 606/223 |
| 5,236,443 | 8/1993 | Sontag | 606/224 |
| 5,693,072 | 12/1997 | Mcintosh | 606/223 |

*Primary Examiner*—Michael Buiz
*Assistant Examiner*—Vikki Trinh
*Attorney, Agent, or Firm*—Townsend & Banta

[57] ABSTRACT

An object of the present invention is to provide a safe surgical needle apparatus, and a surgical needle and a needle holder used therein, which can prevent the medical participants from being erroneously punctured with a tip end of the surgical needle and can permit a smooth tissue penetration of the surgical needle only when performing a suturing work.

In accordance with the present invention, there are provided a surgical needle whose surface is formed from an electrically-insulating material except for its tip end portion and its tail portion to the latter of which a suture can be attached; a needle holder for clamping said tail portion of the surgical needle, in which at least a clamping surface thereof, which comes into contact with the surgical needle, is made of a conductive material and which includes a means for applying an electric current to the portion; and a surgical needle apparatus comprising the afore-mentioned surgical needle and needle holder, and an electric source for supplying an electric current to the surgical needle through the needle holder.

13 Claims, 4 Drawing Sheets

SURGICAL NEEDLE DEVICE

TECHNICAL FIELD

In surgical operations, it is required to suture a body tissue of each organ by using a surgical needle and a suture. This invention relates to a surgical needle, a needle holder for holding the surgical needle and a surgical needle apparatus as a whole system, which are capable of safely performing suturing work in surgical operations.

BACKGROUND ART

Hitherto, the suturing work in surgical operations has been performed by using a surgical needle which has a curved shape like that obtained by bending an ordinary sewing needle and to a tail portion of which a suture is preliminarily attached.

As such surgical needles, there have been eyed-type needles which are capable of attaching and removing a suture at user's end, and eyeless-type needles which are marketed with a suture already attached by makers. Further, surgical needles are classified, according to their shapes, into round needles tapered toward a tip thereof and having a circular cross-section, polygonal needles whose tip end is formed into a lance shape having a triangular cross-section, spatula needles whose tip end is formed into a knife shape, or the like. At present, such various types of the surgical needles have been selectively used depending on a nature of tissue of the organ to be operated or purposes of the suturing work. Any of these surgical needles has usually machined into a very sharp tip so as to allow surgeons to readily perform the tissue penetration thereof even when only a small penetration force is applied thereto by the surgeons.

In the suturing work, the surgical needle is clamped at a tail end thereof by a needle holder which can be manipulated by surgeons. The needle holder is manipulated such that the surgical needle penetrates the tissue and then the tip end thereof protrudes outside the tissue. After the needle holder is removed from the tail end of the surgical needle, the surgical needle is pinched at the tip end by the needle holder and pulled out of the tissue to pass a suture attached thereto through the tissue. Thereafter, the suture is tied for ligation of the tissue and cut near the ligated portion by scissors or the like. The unnecessary used surgical needle and cut suture are discarded. The suturing work is completed by performing these sequential operations.

Since conventional surgical needles have very sharp tip ends, there have frequently occurred such puncture accidents that surgeons or their assistants are erroneously in touch with the tip ends during surgical operations and injured by themselves. In such a case, if patients to be surgically operated are carriers of bacteria and viruses which are infectious through blood, there is a large risk that the surgeons and their assistants are susceptible to these infectious diseases through a very small amount of blood attached to the tip end of the surgical needle. Also, when the used surgical needles, which are contaminated with such blood, are discarded after surgical operations, surgical participants, hospital participants or participants in waste disposal are similarly exposed to risk of accidental infection of the infectious diseases. Recently, this poses a social problem.

Accordingly, all of these participants must take a great care upon handling the surgical needle so as not to be in touch with the tip end thereof.

However, when the needle holder to which the surgical needle is fitted is handed over from the surgical assistant to the surgeon or returned from the surgeon back to the surgical assistant, there is a likelihood that the needle tip impinges against a hand of the surgical assistant or the surgeon, thereby causing puncture accidents. Further, in the case where the surgical operation is associated with complicated suturing work, surgeons have to insert their fingertips into a deep portion in a body of the patient. In this case, the fingertips of the surgeons come into direct contact with the needle tip, thereby also causing the puncture accidents. Thus, even though a great care is taken, the puncture accidents cannot be completely prevented.

In consequence, it have been recently proposed that conventional surgical needles having a blunted tip, i.e., blunt needles, which have been used for suture of specific tissues, are applied to suturing of other tissues. However, many tissues cannot be penetrated by such blunt needles. When it is intended that the blunt needle forcibly penetrates these tissues by applying a large penetration force thereto, the risk of puncture accidents is rather increased in many cases. As a result, this proposal is practically unacceptable to surgeons.

The present invention has been accomplished in view of the afore-mentioned problems.

DISCLOSURE OF THE INVENTION

For example, even though a blunt tip of a metal rod having a diameter on the order of 1 mm is pressed against a tissue of organ, no puncture of the metal rod in the tissue can be caused by applying thereto such a force as exerted in an ordinary suturing work.

Next, in the case where the metal rod is coupled to a conventionally known electric cautery device and pressed against the tissue while a high-frequency current is applied to the metal rod, the tissue, which comes into contact with the metal rod, is caused to be destroyed so that the metal rod readily punctures the tissue.

The reason therefor is suggested such that a water content in the tissue is explosively distilled as soon as it is brought into contact with the tip of the metal rod, so that the tissue is allowed to be destroyed and incised by the pressure of the resulting steam.

The present invention has been attained by taking a hint from the known electric cautery device. That is, in accordance with the present invention, there are provided a surgical needle having a blunt tip and an electrically-insulating material covering a surface thereof except for the blunt tip and a tail portion which are coupled to each other in an electrically continuous manner; a needle holder for clamping the tail portion of the afore-mentioned surgical needle, in which at least a clamping portion which comes into contact with the surgical needle is made of a conductive material and which includes a means for applying an electric current to the portion; and a surgical needle apparatus comprising the surgical needle, the needle holder and an electric source for supplying an electric current to the surgical needle through the needle holder.

BEST MODE FOR CARRYING OUT THE INVENTION

Figure 1:
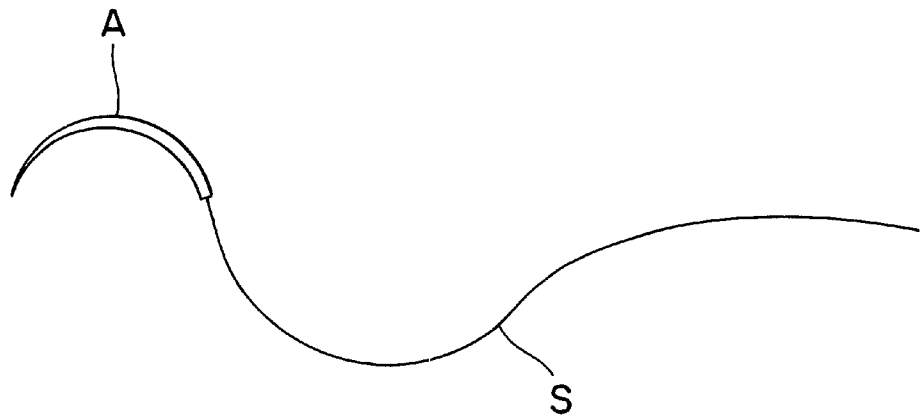
FIG. 1 is a front view of a surgical needle to which a suture is attached.
Figure 2:
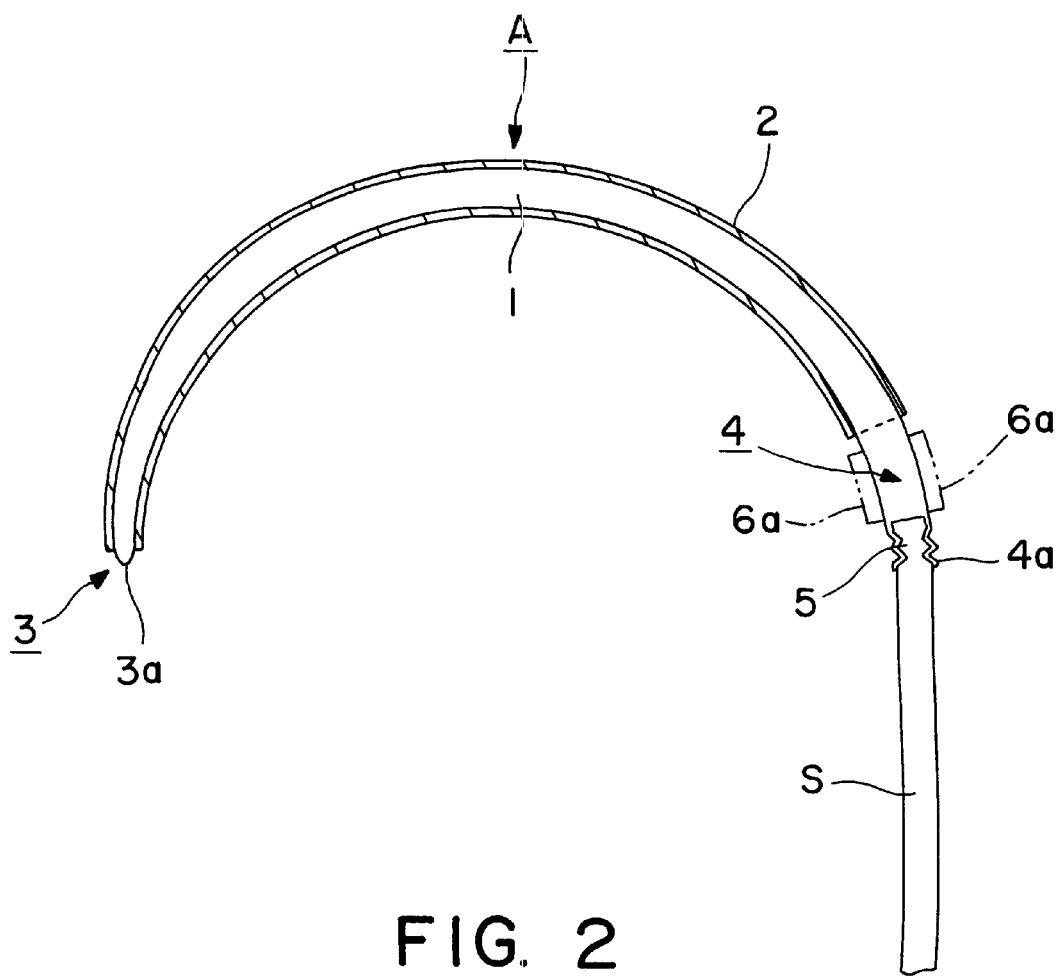
FIG. 2 is an enlarged cross-section of a part of the surgical needle shown in FIG. 1.
Figure 3:
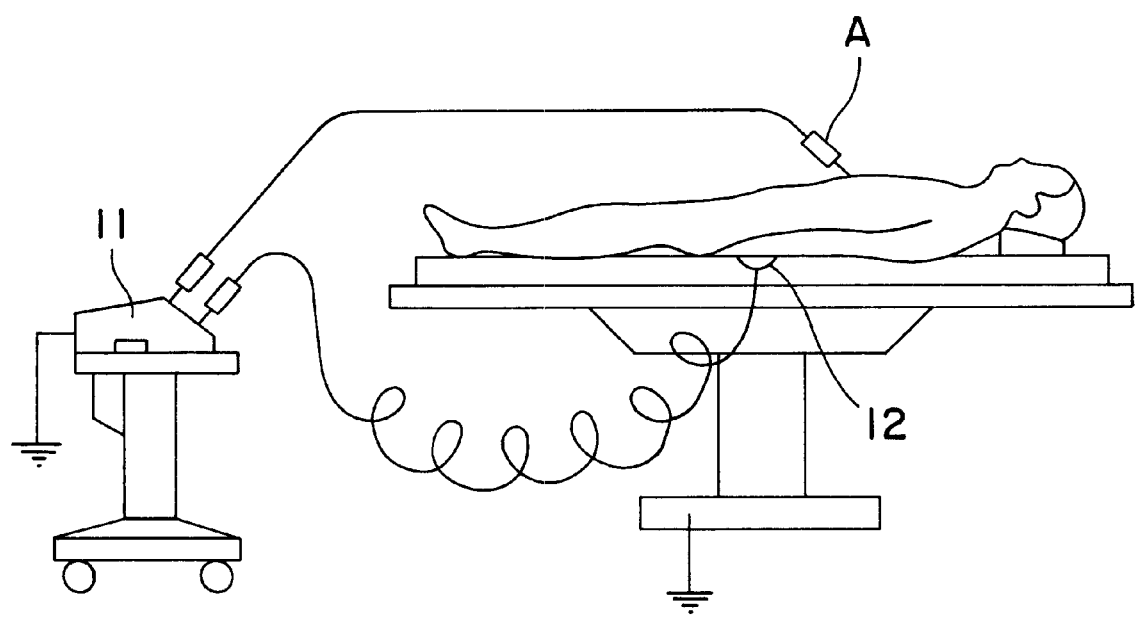
FIG. 3 is a schematic view explaining the state of use of the surgical needle apparatus according to the present invention.
Figure 4:
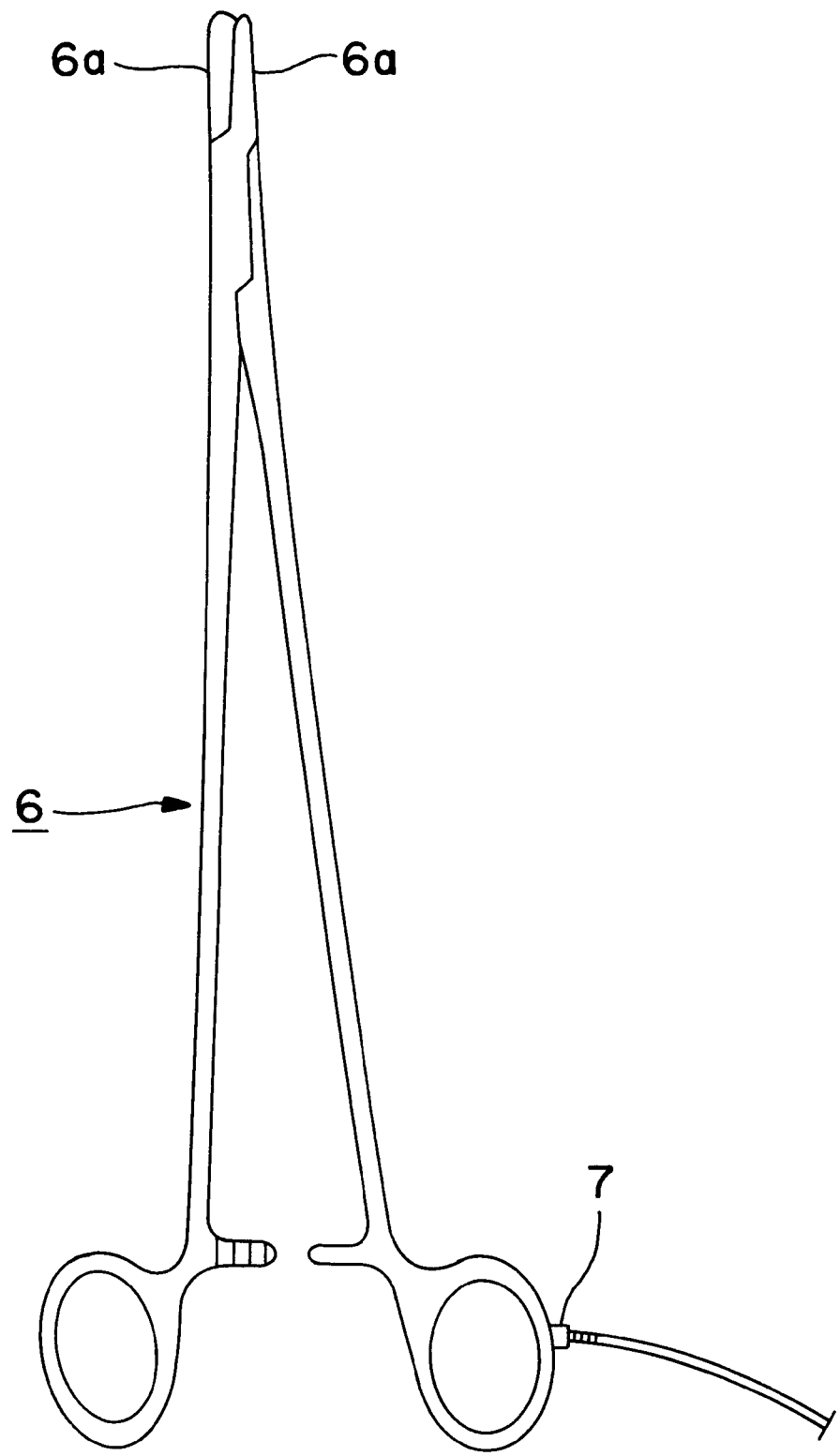
FIG. 4 is a front view of a needle holder.
Figure 5:
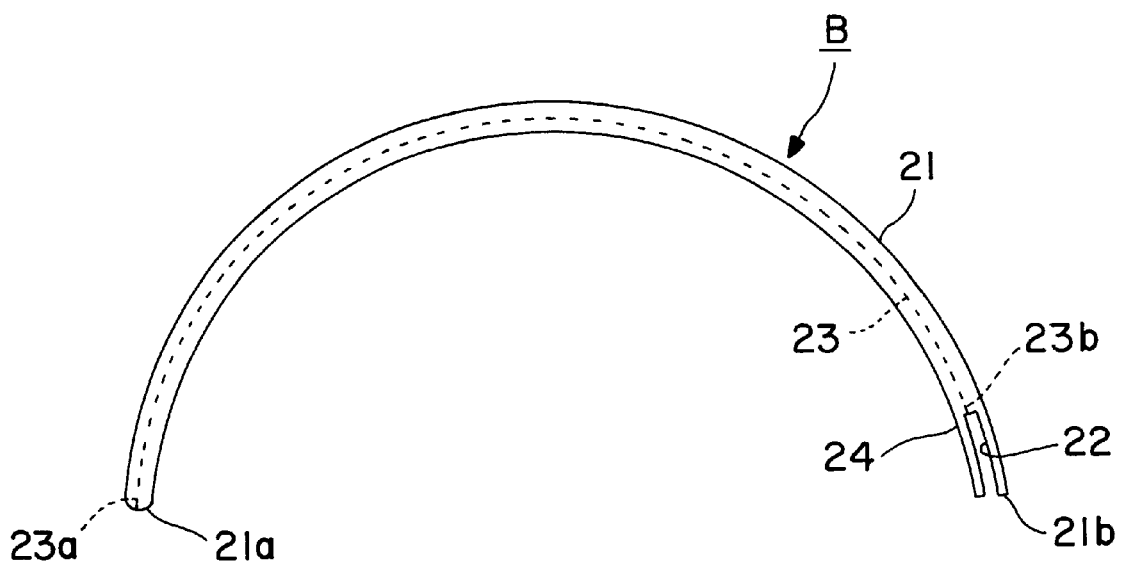
FIG. 5 is a view explaining a surgical needle according to another embodiment of the present invention.

The accompanying drawings illustrate preferred embodiments of a surgical needle, a needle holder and a surgical needle apparatus according to the present invention, in which FIG. 1 shows a front view of the surgical needle to which a suture is attached; FIG. 2 shows an enlarged cross-section of a part of the surgical needle illustrated in FIG. 1; FIG. 3 shows a schematic view explaining the state of use of the surgical needle apparatus according to the present invention; FIG. 4 shows a front view of the needle holder; and FIG. 5 shows a explanatory view of a surgical needle according to another embodiment of the present invention.

First, referring to FIGS. 1 and 2, there are shown a surgical needle A and a suture S. The surgical needle A is of a circular shape in cross section similarly to that of ordinary sewing needles and gradually reduced in its diameter from an intermediate portion thereof towards a tip end thereof so as to provide a tapered tip. Further, the surgical needle is composed of a needle body 1 formed into an arcuate shape as a whole (the needle body is generally made of stainless steel but may be selectively formed from any other metal as far as it can exhibit an electrical conductivity), and an electrically-insulating layer 2 coated on the needle body 1.

The needle body 1 is formed at a tip end portion 3 thereof with a tip 3a which is rounded or blunted so as not to readily stick in surgical rubber gloves or fingertips, and at a tail end 4a thereof with a recessed portion 5 which serves for coupling with the suture S. The suture S is fitted to the needle body 1 by inserting the suture S into the recessed portion 5 and then connecting the suture S to the recessed portion 5 by pressing the recessed portion 5 from outside. The electrically-insulating layer 2 is not provided over the tail portion 4 in order to allow an electric current to be applied to the surgical needle.

The reason why the needle tip of the needle body 1 is formed into a circular shape in cross-section and reduced in its diameter towards the tip and why the electrically-insulating layer 2 is provided up to near the tip 3a (which is not restricted to a rounded or blunted shape but may be of a planar shape or any other shape as far as it makes the needle body less puncturable in tissue) is not only to reduce an contact area of the surgical needle with the tissue of organ so as to cause a small tissue destruction by application of the electric current, but also to facilitate the penetration of the surgical needle A into the tissue while dilating, thereby limiting the tissue destruction to a minimum level.

The electrically-insulating layer 2 may be made of a fluoro-resin and provided over a surface of the needle body 1 except for the tip end portion 3 and the tail portion 4 thereof. Any materials such as other resins, coating materials, rubbers or the like may be used to form the electrically-insulating layer 2. Methods of forming the electrically-insulating layer 2 is not limited to a particular one but the formation thereof may be performed by any method such as baking, coating, adhesion or the like.

Incidentally, the "tip end portion 3" means a tip-side end portion of the needle body 1 which is not covered with the electrically-insulating layer 2 to allow application of an electrical current to the tissue of organ through the tip end portion 3. As long as an electrical current can be applied and the penetration into the tissue can be permitted, the tip end portion 3 has preferably an area as small as possible. It is preferred that the tip 3a of the tip end portion 3 be of a spherical shape. However, the shape of the tip 3a is not limited to the particular one but may be of any other rounded or blunted shape as far as it makes the surgical needle less puncturable in a human skin. In addition, the tip 3a may be larger or conversely smaller in size than the remainder of the tip end portion 3.

On the other hand, the "tail portion 4" means an end portion which includes an outer peripheral surface of the recessed portion 5 to which the suture S is attached, and its adjacent regions (vicinities). Only the outer peripheral surface of the recessed portion 5, i.e., a portion serving for coupling with the suture S, or both the outer peripheral surface of the recessed portion and its adjacent regions may be defined as the tail portion 4 and remain uncovered with the electrically-insulating layer. Alternatively, only the adjacent regions may remain uncovered with the electrically-insulating layer while the outer peripheral surface of the recessed portion may be covered with the electrically-insulating layer. In consequence, in order to apply an electrical current to the needle body 1 through a clamping surface of each clamping piece 6a, 6a attached to a needle holder 6 as shown in FIG. 4 and then apply the electrical current to the tissue of organ through the tip end portion 3 of the surgical needle A, the tail portion 4 may be defined as either a predetermined area extending from the tail end 4a or as a predetermined area adjacent to a given area extending by a certain distance from the tail end 4a and covered with the electrically-insulating layer.

Next, referring to FIGS. 3 and 4, the needle holder 6 as shown in FIG. 4 is composed of a body portion and a connecting terminal 7 which is formed continuously with the body portion and adapted to be connected with an electric cord from an electric source 11 (high-frequency current generator). The electrical current thus introduced from the terminal is supplied to the clamping pieces 6a through the body portion of the needle holder 6. An electrically-insulating layer can be provided on a portion of the needle holder adjacent to but except for clamping surfaces of the clamping pieces 6a (contact surfaces of the surgical needle A and the tail portion 4), or over a surface of the needle holder except for the connecting terminal and the clamping surfaces of the clamping pieces 6a. As materials of the electrically-insulating layer 2, any electrically-insulating materials such as resins, coating materials or rubbers can be used like the case of the surgical needle A. Similarly, baking, coating, adhesion or the like can be used as a method of forming the electrically-insulating layer 2. Further, the body portion itself of the needle holder 6 may be formed from an electrically-insulating material such as resins, and a conductive wire may be embedded in the body portion of the needle holder to supply an electric current from the connecting terminal 7 to the clamping surfaces of the clamping pieces 6.

When surgical operation are actually performed, as shown in FIG. 3, one of the electric cords from the electric source unit is connected to a counter electrode plate 12 disposed on a side of patient and the other of the electric cords is connected to the connecting terminal 7 of the needle holder 6 which clamps a non-insulating portion provided on the tail portion 4 of the surgical needle A, in the same manner as in the case of conventional electric cautery devices. When the surgical needle A is stuck in the tissue to conduct a suturing work, the surgeon depresses a foot switch (not shown) for supplying an electric current, and press the surgical needle A into the tissue while continuing the supply of electric current, so that the surgical needle A readily penetrates the tissue, thereby accomplishing an ideal perforation of the tissue.

After the tip end portion 3 of the surgical needle A penetrates the tissue of organism and emerges out of a surface of the tissue, the surgeon releases his foot from the foot switch to terminate the supply of an electric current to the surgical needle, and performs an ordinary suturing work. That is, although the surgical needle A has electrically-exposed portions in the tip end portion 3 and the tail portion 4, it is prevented that an undesired flow of electric current between the tail portion and the tissue of organism is caused. This is because the tip end portion completely penetrates the tissue and emerges therefrom before the tail portion comes into contact with the tissue of organism and then, after the foot switch is released, the needle tip protruded from the surface of the tissue is clamped by the same needle holder 6 to permit the surgical needle A to be pulled out of the tissue.

Meanwhile, in accordance with the present invention, conventional needle holders entirely made of a conductive material can also be used. In this case, in order to avoid undesired flow of electric current between the surgeon and handles of the needle holder, surgical rubber gloves exhibiting an electrically-insulating property are preferably used. Also, care should be taken to keep the needle holder from the patient.

In FIG. 5, there is shown a surgical needle according to another embodiment of the present invention, in which the surgical needle according to the preceding embodiment is modified such that the thickness of the electrically-insulating layer 2 is extremely increased and the needle body 1 serves only for providing an electrical conductivity. As is shown in FIG. 5 the surgical needle B of this embodiment is made substantially of an insulating material such as plastics, and comprises an arcuate needle body 21 having a circular cross-section and made of a plastic material such as polycarbonates, a conductive wire 23 made of metal or the like and embedded in the needle body 21. The needle body 21 has a tip 21a molded into a semi-spherical shape such that one end 23a of the afore-mentioned conductive wire 23 emerges out of a surface thereof.

The needle body 21 is formed at a tail end 21b thereof with a recessed portion 22 to which a suture (not shown) can be fitted. The opposite end 23b of the conductive wire 23 emerges from an inner surface of the recessed portion 22. By providing a metal-plated layer over a region from the inner surface of the recessed portion 22 up to an outer peripheral surface of the tail portion 24, the tip end portion of the surgical needle B can be electrically connected with the outer peripheral surface of the tail portion 24. Alternatively, such an electrical connection between the tip end portion and the tail portion can be achieved by such a structure in which the embedded conductive wire 23 emerges from the outer peripheral surface of the tail portion 24.

According to the latter embodiment, there is an advantage that the production of such a surgical needle is less expensive as compared with ordinary ones having a main needle body made of metal. In addition, since the tip of the surgical needle is made of a plastic material, such a surgical needle is unlikely to stick in the tissue in an ordinary state, thereby rendering the surgical needle much safe.

Incidentally, the rigidity of the surgical needle B can be readily adjusted by varying the sort of plastic material used for the needle body 21 and the strength and the size of the conductive wire 23. Further, by varying the electrical conductivity and the size of the conductive wire, there can be provided surgical needles having various penetrating properties which are adaptable to various surgical operations.

Meanwhile, the foregoing explanations are made with respect to eyeless-type surgical needles. Needless to say, the present invention is also applicable to eyed-type surgical needles to which a suture can be removably attached.

In the afore-mentioned arrangement of the present invention, only the narrow tip end portion of the surgical needle, which comes into contact with the tissue of organ, can serve for applying an electric current thereto. Accordingly, while destroying only a small portion of the tissue contacting the tip end portion, the surgical needle can be readily inserted into the tissue by applying an extremely small penetration force. At this time, a water content is allowed to evaporate spontaneously and explosively from the small portion of the tissue contacting the tip end portion of the surgical needle, so that only a locally-limited destruction of the tissue is caused. As a result, there occurs no burn expanded to a surrounding portion of the tissue contacting the tip end portion of the surgical needle. Further, the tissue can be subjected to an appropriate coagulation by the application of the electric current, thereby enabling simultaneous hemostasis at a penetrated portion of the tissue. There is no hemorrhage from the bore of the tissue formed by the needle penetration, thereby causing an ideal perforation of the tissue when a suture is passed therethrough.

Accordingly, even though the tip of the surgical needle is formed into a blunt shape to render it less puncturable, inherent functions of the surgical needle are not lost and it can rather exhibit extremely excellent tissue-penetrating properties. Further, since the surgical needle according to the present invention can be used to effect the tissue penetration only during application of electric current, there occurs no erroneous puncture accidents during no application of electric current, thereby providing a safe surgical needle and a safe surgical needle apparatus. Also, even though the tip of the surgical needle erroneously comes into contact with a part of a body of the surgeon during surgical operations, there is caused no electric current flow between the surgical needle and the body of the surgeon because the surgeon is in no contact with a counter electrode plate, so that the surgeon can be safely protected from being punctured with the surgical needle.

Industrial Applicability

As described in detail above, a surgical needle, a needle holder and a surgical needle apparatus comprising these members, according to the present invention, can be used to suture the tissue of each organ in surgical operations by using the surgical needle and a suture.

What is claimed is:

1. A surgical needle handled with a needle holder connected with an electrice source comprising:

a blunt tip;

a tail portion which could be held with the needle holder; and a needle body extending between the blunt tip and tail portion, wherein an electrically-insulating material is provided over a surface of the needle body, and said blunt tip being electrically coupled with said tail portion.

2. A surgical needle as claimed in claim 1, wherein an electrically-insulating layer is formed over a surface of a main needle body made of a conductive material except said blunt tip and said tail portion.

3. A surgical needle as claimed in claim 1, wherein a conductive wire is embedded within the needle body made of an electrically-insulating material.

4. A surgical needle as claimed in claim 1, wherein said blunt tip is constituted by a part of a spherical surface.

5. A surgical needle as claimed in claim 1, wherein said tail portion, which is coupled with said blunt tip in an electrically continuous manner, is provided over a predetermined range extending from a tail end of the surgical needle.

6. A surgical needle as claimed in claim 1, wherein said tail portion, which is coupled with said blunt tip in an electrically continuous manner, is provided over a predetermined range adjacent to a given region extending from a tail end of the surgical needle.

7. A needle holder for clamping said tail portion of the surgical needle according to claim 1, comprising:
   a clamping surface which comes into contact with the surgical needle clamped and is made of a conductive material;
   a means for applying an electric current to said clamping surface; and
   an insulating material provided over a surface thereof in close proximity to said clamping surface.

8. A needle holder for clamping said tail portion of the surgical needle according to claim 1, comprising:
   a clamping surface which comes into contact with the surgical needle to be clamped and is made of a conductive material;
   a means for applying an electric current to said clamping surface; and
   an insulating material provided over a surface thereof except for said clamping surface and a connecting terminal.

9. The needle holder of claim 7, wherein said means for applying an electric current to the surgical needle is composed of a body of the needle holder made of a conductive material and/or a conductive wire embedded within a body of the needle holder made of an insulating material, and a connecting terminal continuously formed on the body of the needle holder.

10. A surgical needle apparatus comprising:
    a surgical needle whose surface, except for a tip end portion and a tail portion thereof, is formed from an electrically-insulating material, said tip end portion being coupled with said tail portion in an electrically continuous manner;
    a needle holder for clamping said tail portion of the surgical needle; and
    an electric source for supplying an electric current through said needle holder.

11. The needle holder of claim 8, wherein said means for applying an electric current to the surgical needle is composed of a body of the needle holder made of a conductive material and/or a conductive wire embedded within a body of the needle holder made of an insulating material, and a connecting terminal continuously formed on the body of the needle holder.

12. A method of decreasing the transmission of infectious diseases caused by accidental needle stick during suturing of tissues of the body, comprising the steps of:
    piercing the tissues of a body with a suture needle having a blunt tip which is electrically connected to a means of supplying a high frequency current to the needle,
    passing a current from the means of supplying a high frequency current to the blunt tip of the needle in an amount sufficient to cause the tissue in contact with the blunt tip of the needle to vaporize and permit the needle to penetrate tissues of the body.

13. The method of decreasing the transmission of infectious diseases caused by accidental needle stick during suturing of tissues of the body of claim 12, wherein the means of supplying a high frequency current is electrically connected to a needle holder which in turn is electrically connected to a conductive portion of the surgical needle, and wherein a sufficiently high frequency current is passed from the means for generating high frequency current to the needle via the needle holder in order to effect penetration of the blunt tip of the needle through tissues of the body.

* * * * *

UNITED STATES PATENT AND TRADEMARK OFFICE
CERTIFICATE OF CORRECTION

PATENT NO. : 6,159,233

DATED : December 12, 2000

INVENTOR(S) : Y. Matsuzawa

It is certified that error appears in the above-identified patent and that said Letters Patent is hereby corrected as shown below:

On the Title Page, Item [54] and column 1, line 1 should read ---- Surgical Needle, Needle Holder, And Surgical Needle Apparatus -----.

Signed and Sealed this

Twenty-ninth Day of May, 2001

*Attest:*

NICHOLAS P. GODICI

*Attesting Officer*    Acting Director of the United States Patent and Trademark Office